(12) United States Patent
Krizman et al.

(10) Patent No.: US 8,728,753 B2
(45) Date of Patent: May 20, 2014

(54) METHODS FOR MEASURING THE LEVEL OF INSULIN-LIKE GROWTH FACTOR 1 RECEPTOR (IGF1R) PROTEIN USING SRM/MRM ASSAY

(75) Inventors: David B. Krizman, Gaithersburg, MD (US); Todd Hembrough, Gaithersburg, MD (US); Sheeno Thyparambil, Frederick, MD (US)

(73) Assignee: Expression Pathology Incorporated, Rockville, MD (US)

( * ) Notice: Subject to any disclaimer, the term of this patent is extended or adjusted under 35 U.S.C. 154(b) by 0 days.

(21) Appl. No.: 13/529,875

(22) Filed: Jun. 21, 2012

(65) Prior Publication Data
US 2012/0302650 A1  Nov. 29, 2012

Related U.S. Application Data

(63) Continuation of application No. PCT/US2010/061924, filed on Dec. 22, 2010.

(60) Provisional application No. 61/289,378, filed on Dec. 22, 2009.

(51) Int. Cl.
*C12Q 1/37*  (2006.01)

(52) U.S. Cl.
USPC ............................................. 435/23

(58) Field of Classification Search
None
See application file for complete search history.

(56) References Cited

U.S. PATENT DOCUMENTS 7,473,532 B2 *  1/2009  Darfler et al. .................. 435/7.2

OTHER PUBLICATIONS

Gallen S, et al. Molecular and Cellular Proteomics, 11(12):1709-1723, 2012.*

* cited by examiner

*Primary Examiner* — Robert Landsman
(74) *Attorney, Agent, or Firm* — Perkins Coie LLP

(57) ABSTRACT

Peptides from the Insulin-Like Growth Factor 1 Receptor (IGF-1R) protein are provided that are particularly advantageous for quantifying the IGF-1 R protein directly in biological samples, such as samples fixed in formalin. The ionization characteristics of the peptides also are disclosed. The peptides may be used in Selected Reaction Monitoring (SRM) mass spectrometry methods, also referred to Multiple Reaction Monitoring (MRM) mass spectrometry methods. The samples are chemically preserved and fixed, such as tissues and cells treated with formaldehyde containing agents/fixatives including formalin-fixed tissue/cells, formalin fixed/paraffin embedded (FFPE) tissue/cells, FFPE tissue blocks and cells from those blocks, and tissue culture cells that have been formalin fixed and or paraffin embedded. A protein sample may be prepared from the biological sample and the IGF-IR protein is quantitated by the method of SRM/MRM mass spectrometry by quantitating one or more of the described peptides. These peptides can be quantitated in either modified or unmodified form. An example of a modified form of an IGF-1 R peptide is phosphorylation of a tyrosine, threonine, serine, and/or other amino acid residues within the peptide sequence.

13 Claims, 2 Drawing Sheets

A) Demonstration of SRM/MRM Signature Peak for this IGF-1R Peptide in a Liquid Tissue Lysate from Formalin Fixed Cancer Tissue

METHODS FOR MEASURING THE LEVEL OF INSULIN-LIKE GROWTH FACTOR 1 RECEPTOR (IGF1R) PROTEIN USING SRM/MRM ASSAY

This application is a continuation of International Application No. PCT/US2010/061924, filed Dec. 22, 2010, which claims the benefit of U.S. Provisional Application 61/289,378, filed Dec. 22, 2009, both of which are entitled "Insulin-Like Growth Factor 1 Receptor (IGF1R) Protein SRM Assay" and name as an inventor David B. Krizman; each of which applications is herein incorporated by reference in its entirety.

INTRODUCTION

Specific peptides derived from subsequences of the Insulin-Like Growth Factor 1 Receptor protein and which will be referred to as IGF-1R, and which can also be referred to as CD221 protein, are provided. The peptide sequence and fragmentation/transition ions for each peptide are particularly useful in a mass spectrometry-based Selected Reaction Monitoring (SRM), which can also be referred to as a Multiple Reaction Monitoring (MRM) assay, and will be referred to as SRM/MRM. The use of one such peptide for SRM/MRM quantitative analysis of the IGF-1R protein is described.

This SRM/MRM assay can be used to measure relative or absolute quantitative levels of one or more of the specific peptides from the IGF-1R protein and therefore provide a means of measuring the amount of the IGF-1R protein in a given protein preparation obtained from a biological sample by mass spectrometry.

More specifically, the SRM/MRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by references in their entirety. The methods described in U.S. Pat. No. 7,473,532 may conveniently be carried out using Liquid Tissue™ reagents and protocol available from Expression Pathology Inc. (Rockville, Md.).

The most widely and advantageously available form of tissues from cancer patients tissue is formalin fixed, paraffin embedded tissue. Formaldehyde/formalin fixation of surgically removed tissue is by far and away the most common method of preserving cancer tissue samples worldwide and is the accepted convention for standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the IGF-1R protein within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

SUMMARY

The assays described herein measure relative or absolute levels of specific unmodified peptides from the IGF-1R protein and also can measure absolute or relative levels of specific modified peptides from the IGF-1R protein. Examples of modifications include phosphorylated amino acid residues and glycosylated amino acid residues that are present on the peptides.

Relative quantitative levels of the IGF-1R protein are determined by the SRM/MRM methodology for example by comparing SRM/MRM signature peak areas (e.g., signature peak area or integrated fragment ion intensity) of an individual IGF-1R peptide in different samples. Alternatively, it is possible to compare multiple SRM/MRM signature peak areas for multiple IGF-1R signature peptides, where each peptide has its own specific SRM/MRM signature peak, to determine the relative IGF-1R protein content in one biological sample with the IGF-1R protein content in one or more additional or different biological samples. In this way, the amount of a particular peptide, or peptides, from the IGF-1R protein, and therefore the amount of the IGF-1R protein, is determined relative to the same IGF-1R peptide, or peptides, across 2 or more biological samples under the same experimental conditions. In addition, relative quantitation can be determined for a given peptide, or peptides, from the IGF-1R protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the IGF-1R protein, and therefore the amount of the IGF-1R protein, is determined relative one to another within the same sample. These approaches generate quantitation of an individual peptide, or peptides, from the IGF-1R protein to the amount of another peptide, or peptides, between samples and within samples wherein the amounts as determined by peak area are relative one to another, regardless of the absolute weight to volume or weight to weight amounts of the IGF-1R peptide in the protein preparation from the biological sample. Relative quantitative data about individual signature peak areas between different samples are normalized to the amount of protein analyzed per sample. Relative quantitation can be performed across many peptides from multiple proteins and the IGF-1R protein simultaneously in a single sample and/or across many samples to gain insight into relative protein amounts, one peptide/protein with respect to other peptides/proteins.

Absolute quantitative levels of the IGF-1R protein are determined by, for example, the SRM/MRM methodology whereby the SRM/MRM signature peak area of an individual peptide from the IGF-1R protein in one biological sample is compared to the SRM/MRM signature peak area of a spiked internal standard. In one embodiment, the internal standard is a synthetic version of the same exact IGF-1R peptide that contains one or more amino acid residues labeled with one or more heavy isotopes. Such isotope labeled internal standards are synthesized so that when analyzed by mass spectrometry it generates a predictable and consistent SRM/MRM signature peak that is different and distinct from the native IGF-1R peptide signature peak and which can be used as a comparator peak. Thus when the internal standard is spiked into a protein preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer. Assays of protein levels (e.g., IGF-1R levels) can also be used to diagnose the stage of cancer in a patient or subject diagnosed with cancer by employing the IGF-1R levels. Levels or amounts of proteins or peptides can be defined as the quantity expressed in moles, mass or weight of a protein or peptide determined by the SRM/MRM assay. The level or amount may be normalized to total the level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding IGF-1R can thus be used to aid in determining stage or grade of a cancer by correlating the level of the IGF-1R protein (or fragment peptides of the IGF-1R protein) with levels observed in normal tissues. Once the stage and/or grade, and/or IGF-1R protein expression characteristics of the cancer has been determined, that information can be matched to a list of therapeutic agents (chemical and biological) developed to specifically treat cancer tissue that is characterized by, for example, abnormal expression of the protein or protein(s) (e.g., IGF-1R) that were assayed. Matching information from an IGF-1R protein assay to a list of therapeutic agents that specifically targets, for example, the IGF-1R protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

DETAILED DESCRIPTION

Figure 1:
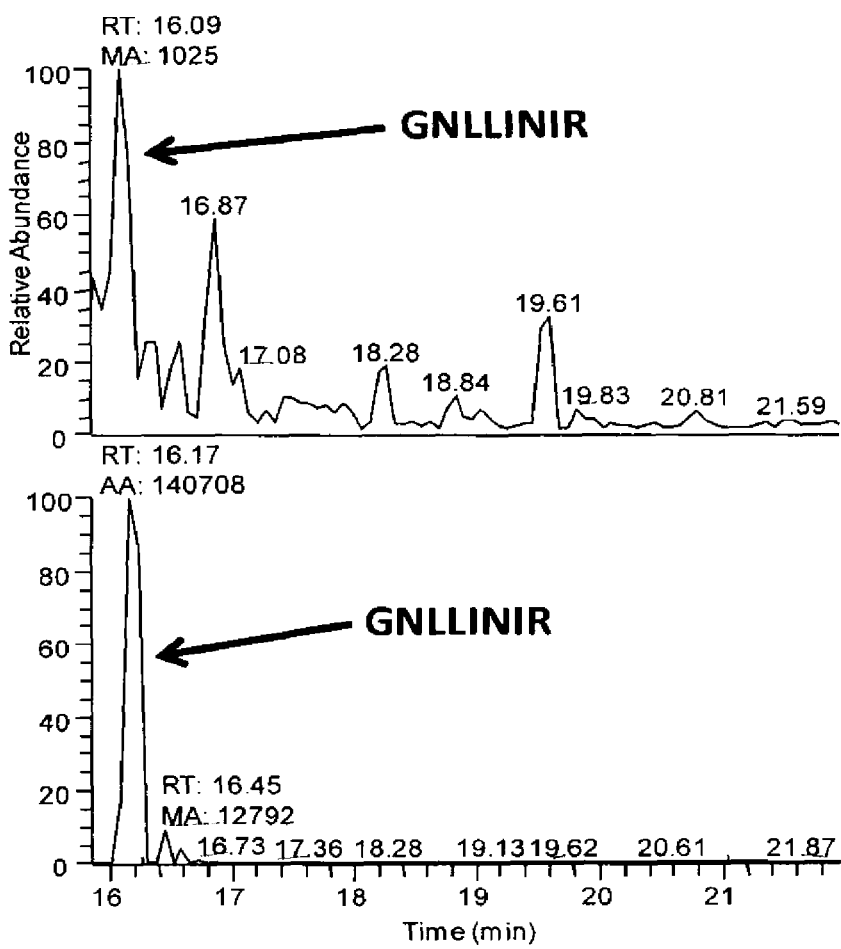
FIGS. 1A and 1B show an example of an SRM/MRM assay of a single peptide from the IGF-IR protein performed on Liquid Tissue™ lysates with quantitation of the IGF-1 R peptide conducted on a triplequadrupole mass spectrometer.
Figure 1:
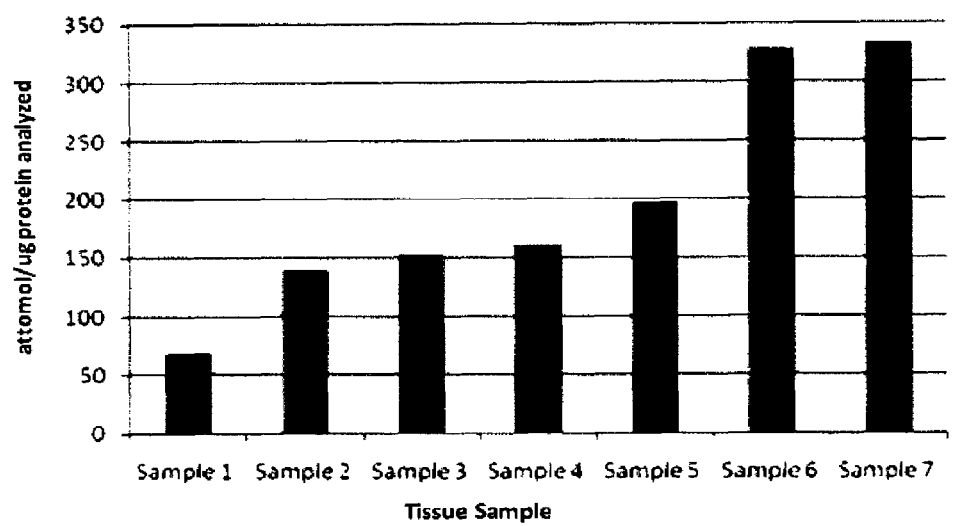

In principle, any predicted peptide derived from IGF-1R protein, prepared for example by digesting with a protease of known specificity (e.g. trypsin), can be used as a surrogate reporter to determine the abundance of IGF-1R protein in a sample using a mass spectrometry-based SRM/MRM assay. Similarly, any predicted peptide sequence containing an amino acid residue at a site that is known to be potentially modified in IGF-1R protein also might potentially be used to assay the extent of modification of IGF-1R protein in a sample.

IGF-1R fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is heated in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent). Following heat treatment the tissue/biological sample is treated with one or more proteases, including but not limited to trypsin, chymotrypsin, pepsin, and endoproteinase Lys-C for a time sufficient to disrupt the tissue and cellular structure of said biological sample and to liquefy said sample (e.g., a period of time from 30 minutes to 24 hours at a temperature from 37° C. to 65° C.). The result of the heating and proteolysis is a liquid, soluble, dilutable biomolecule lysate.

Surprisingly, it was found that many potential peptide sequences from the IGF-1R protein are unsuitable or ineffective for use in mass spectrometry-based SRM/MRM assays for reasons that are not immediately evident. As it was not possible to predict the most suitable peptides for MRM/SRM assay, it was necessary to experimentally identify modified and unmodified peptides in actual Liquid Tissue™ lysates to develop a reliable and accurate SRM/MRM assay for the IGF-1R protein. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware.

IGF-1R peptides found in various embodiments of this disclosure (e.g., Tables 1 and 2) were derived from the IGF-1R protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the IGF-1R protein that are detected and analyzed by mass spectrometry. Identification of a specific preferred subset of peptides for mass-spectrometric analysis is based on: 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

TABLE I

| SEQ ID NO. | Peptide Sequence |
|---|---|
| SEQ ID NO: 1 | GNLLINIR |
| SEQ ID NO: 2 | AGKMYFAFNPK |
| SEQ ID NO: 3 | AVTLTMVENDHIRGAKSEILYIR |
| SEQ ID NO: 4 | DVEPGILLHGLK |
| SEQ ID NO: 5 | ECGDLCPGTMEEKPMCEK |
| SEQ ID NO: 6 | EEAEYR |
| SEQ ID NO: 7 | ERTVISNLRPFTLYR |
| SEQ ID NO: 8 | GPCCACPKTEAEKQAEK |
| SEQ ID NO: 9 | GVVKDEPETRVAIK |
| SEQ ID NO: 10 | IPIRKYADGTIDIEEVTENPK |
| SEQ ID NO: 11 | KTKTIDSVTSAQMLQGCTIFK |
| SEQ ID NO: 12 | LCVSEIYRMEEVTGTKGR |
| SEQ ID NO: 13 | LFYNYALVIFEMTNLKDIGLYNLR |
| SEQ ID NO: 14 | LNRLNPGNYTAR |
| SEQ ID NO: 15 | MIQMAGEIADGMAYLNANK |
| SEQ ID NO: 16 | NADLCYLSTVDWSLILDAVSNNYIVGNK |
| SEQ ID NO: 17 | PDNCPDMLFELMR |
| SEQ ID NO: 18 | PMCEKTTINNEYNYRCWTTNR |
| SEQ ID NO: 19 | PPKECGDLCPGTMEEK |
| SEQ ID NO: 20 | SEILYIRTNASVPSIPLDVLSASNSSSQLIVK |
| SEQ ID NO: 21 | TEAEKQAEKEEAEYR |
| SEQ ID NO: 22 | TEVCGGEKGPCCACPKTEAEK |
| SEQ ID NO: 23 | TGYENFIHLIIALPVAVLLIVGGLVIMLYVFHRKR |
| SEQ ID NO: 24 | TIDSVTSAQMLQGCTIFK |
| SEQ ID NO: 25 | TKTIDSVISAQMLQGCTIFKGNLLINIR |
| SEQ ID NO: 26 | TTINNEYNYRCWTTNRCQK |
| SEQ ID NO: 27 | VFENFLHNSIFVPRPERK |
| SEQ ID NO: 28 | WNPPSLPNGNLSYYIVR |
| SEQ ID NO: 29 | WPEPENPNGLILMYEIK |
| SEQ ID NO: 30 | YADGTIDIEEVTENPKTEVCGGEK |
| SEQ ID NO: 31 | YGGAKLNRLNPGNYTAR |
| SEQ ID NO: 32 | YGSQVEDQRECVSR |
| SEQ ID NO: 33 | ACTENNECCHPECLGSCSAPDNDTACVACR |
| SEQ ID NO: 34 | DLAARNCMVAEDFTVK |
| SEQ ID NO: 35 | DLISFTVYYKEAPFK |
| SEQ ID NO: 36 | EKITMSRELGQGSFGMVYEGVAK |

TABLE I-continued

| SEQ ID NO. | Peptide Sequence |
|---|---|
| SEQ ID NO: 37 | ELGQGSFGMVYEGVAKGVVK |
| SEQ ID NO: 38 | FPKLTVITEYLLLFR |
| SEQ ID NO: 39 | FVMEGGLLDK |
| SEQ ID NO: 40 | GNNIASELENFMGLIEVVTGYVK |
| SEQ ID NO: 41 | GWKLFYNYALVIFEMTNLKDIGLYNLR |
| SEQ ID NO: 42 | HYYYAGVCVPACPPNTYR |
| SEQ ID NO: 43 | IDIHSCNHEAEKLGCSASNFVFAR |
| SEQ ID NO: 44 | YRPPDYR |
| SEQ ID NO: 45 | KYGGAK |
| SEQ ID NO: 46 | LENCTVIEGYLHILLISKAEDYRSYR |
| SEQ ID NO: 47 | LNPGNYTARIQATSLSGNGSWTDPVFFYVQAK |
| SEQ ID NO: 48 | MEEVTGTKGRQSK |
| SEQ ID NO: 49 | NGSQSMYCIPCEGPCPK |
| SEQ ID NO: 50 | NGSQSMYCIPCEGPCPKVCEEEK |
| SEQ ID NO: 51 | NITRGAIR |
| SEQ ID NO: 52 | NNGER |
| SEQ ID NO: 53 | NNGERASCESDVLHFTSTTTSK |
| SEQ ID NO: 54 | QPQDGYLYR |
| SEQ ID NO: 55 | QPQDGYLYRHNYCSKDK |
| SEQ ID NO: 56 | QSKGDINTRNNGER |
| SEQ ID NO: 57 | RGNNIASELENFMGLIEVVTGYVKIR |
| SEQ ID NO: 58 | SRNTTAADTYNITDPEELETEYPFFESR |
| SEQ ID NO: 59 | TNASVPSIPLDVLSASNSSSQLIVK |
| SEQ ID NO: 60 | TVISNLRPFTLYR |
| SEQ ID NO: 61 | VAGLESLGDLFPNLTVIRGWK |
| SEQ ID NO: 62 | WPEPENPNGLILMYEIK |
| SEQ ID NO: 63 | ALPLPQSSTC |
| SEQ ID NO: 64 | ASCESDVLHFTSTTTSKNRIIITWHR |
| SEQ ID NO: 65 | IIITWHR |
| SEQ ID NO: 66 | FVMEGGLLDK |
| SEQ ID NO: 67 | HYYYAGVCVPACPPNTYRFEGWR |
| SEQ ID NO: 68 | NDYQQLKRLENCTVIEGYLHILLISK |
| SEQ ID NO: 69 | NGSQSMYCIPCEGPCPKVCEEEKK |
| SEQ ID NO: 70 | NTTAADTYNITDPEELETEYPFFESR |
| SEQ ID NO: 71 | DIYETDYYR |
| SEQ ID NO: 72 | DIY[Phosphoryl]ETDYYR |
| SEQ ID NO: 73 | DIY[Phosphoryl]ETDY[Phosphoryl]YR |
| SEQ ID NO: 74 | DIY[Phosphoryl]ETDYY[Phosphoryl]R |
| SEQ ID NO: 75 | DIYETDY[Phosphoryl]Y[Phosphoryl]R |

TABLE I-continued

| Table 1 SEQ ID NO. | Peptide Sequence |
|---|---|
| SEQ ID NO: 76 | DIYETDY[Phosphoryl]YR |
| SEQ ID NO: 77 | DIYETDYY[Phosphoryl]R |
| SEQ ID NO: 78 | DIY[Phosphoryl]ETDY[Phosphoryl]Y[Phosphoryl]R |

TABLE 2

| Table 2 SEQ ID NO.: | Peptide sequence | Mono Isotopic Mass | Precursor Charge State | Precursor m/z | Transition m/z | Ion Type |
|---|---|---|---|---|---|---|
| SEQ ID NO: 1 | GNLLINIR | 911.555 | 2 | 456.784 | 515.33 | y4 |
| | | | 2 | 456.784 | 628.41 | y5 |
| | | | 2 | 456.784 | 741.5 | y6 |

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers however may be the best type of mass spectrometer for conducting global profiling of peptides. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the IGF-1R protein.

In one embodiment, the IGF-1R tryptic peptides identified as useful in the determination of absolute or relative amounts of the IGF-1R receptor include one or more, two or more, three or more, four or more, five or more, six or more, eight or more, or ten or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:38, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, eight or more, or ten or more of those peptides recited in Table 1, and particularly combinations with the peptide found in Table 2) are candidates for use in quantitative SRM/MRM assay for the IGF-1R protein in human biological samples, including directly in formalin fixed patient tissue.

The IGF-1R tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the IGF-1R protein in formalin fixed tissue. Further data analysis of these experiments indicated no preference is observed for any specific peptides from any specific organ site. Thus, each of these peptides is believed to be suitable for conducting SRM/MRM assays of the IGF-1R protein on a Liquid Tissue™ lysate from any formalin fixed tissue originating from any biological sample or from any organ site in the body.

In one embodiment the peptides in Table 1, or any combination of those peptides (e.g., one or more, two or more, three or more, four or more, five or more, six or more, eight or more, or ten or more of those peptides recited in Table 1, and particularly combinations with the peptide also found in Table 2) are assayed by methods that do not rely upon mass spectroscopy, including, but not limited to, immunological methods (e.g., Western blotting or ELISA). Regardless of how information directed to the amount of the peptide(s) (absolute or relative) is obtained, the information may be employed in any of the methods described herein, including indicating (diagnosing) the presence of cancer in a subject, determining the stage/grade/status of the cancer, providing a prognosis, or determining the therapeutics or treatment regimen for a subject/patient.

Embodiments of the present disclosure include compositions comprising one or more, two or more, three or more, four or more, five or more, six or more, eight or more, or ten or more of the peptides in Table 1. In some embodiments, the compositions comprise the peptide in Table 2. Compositions comprising peptides may include one or more, two or more, three or more, four or more, five or more, six or more, eight or more, or ten or more peptides that are isotopically labeled. Each of the peptides may be labeled with one or more isotopes selected independently from the group consisting of $^{18}O$, $^{17}O$, $^{34}S$, $^{15}N$, $^{13}C$, $^{2}H$ or combinations thereof. Compositions comprising peptides from the IGF-1R protein, whether isotope labeled or not, do not need to contain all of the peptides from that protein (e.g., a complete set of tryptic peptides). In some embodiments the compositions do not contain one or more, two or more, three or more, four or more, five or more, six or more, eight or more, or ten or more peptides from IGF-1R, and particularly peptides appearing in Table 1 or Table 2. Compositions comprising peptides may be in the form of dried or lyophilized materials, liquid (e.g., aqueous) solutions or suspensions, arrays, or blots.

An important consideration for conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the IGF-1R protein it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific IGF-1R peptides, may include one or more of the mono isotopic mass of the peptide, its precursor charge state, the precursor m/z value, the m/z transition ions, and the ion type of each transition ion. Additional peptide information that may be used to develop an SRM/MRM assay for the IGF-1R protein is shown by example for one (1) of the IGF-1R peptides from the list in Table 1 and is shown in Table 2. Similar additional information described for this one (1) IGF-1R peptide shown by example in Table 2 may be prepared, obtained, and applied to the analysis of the other peptides contained in Table 1.

The method described below was used to: 1) identify candidate peptides from the IGF-1R protein that can be used for a mass spectrometry-based SRM/MRM assay for the IGF-1R protein, 2) develop individual SRM/MRM assay, or assays, for target peptides from the IGF-1R protein in order to correlate and 3) apply quantitative assays to cancer diagnosis and/or choice of optimal therapy.

Assay Method

1. Identification of SRM/MRM candidate fragment peptides for the IGF-1R protein
   a. Prepare a Liquid Tissue™ protein lysate from a formalin fixed biological sample using a protease or proteases, (that may or may not include trypsin), to digest proteins
   b. Analyze all protein fragments in the Liquid Tissue™ lysate on an ion trap tandem mass spectrometer and identify all fragment peptides from the IGF-1R protein, where individual fragment peptides do not contain any peptide modifications such as phosphorylations or glycosylations
   c. Analyze all protein fragments in the Liquid Tissue™ lysate on an ion trap tandem mass spectrometer and identify all fragment peptides from the IGF-1R protein that carry peptide modifications such as for example phosphorylated or glycosylated residues
   d. All peptides generated by a specific digestion method from the entire, full length IGF-1R protein potentially can be measured, but preferred peptides used for development of the SRM/MRM assay are those that are identified by mass spectrometry directly in a complex Liquid Tissue™ protein lysate prepared from a formalin fixed biological sample
   e. Peptides that are specifically modified (phosphorylated, glycosylated, etc.) in patient tissue and which ionize, and thus detected, in a mass spectrometer when analyzing a Liquid Tissue™ lysate from a formalin fixed biological sample are identified as candidate peptides for assaying peptide modifications of the IGF-1R protein 2. Mass Spectrometry Assay for Fragment Peptides from IGF-1R Protein
   a. SRM/MRM assay on a triple quadrupole mass spectrometer for individual fragment peptides identified in a Liquid Tissue™ lysate is applied to peptides from the IGF-1R protein
      i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
      ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
      iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer b. Perform SRM/MRM analysis so that the amount of the fragment peptide of the IGF-1R protein that is detected, as a function of the unique SRM/MRM signature peak area from an SRM/MRM mass spectrometry analysis, can indicate both the relative and absolute amount of the protein in a particular protein lysate.
  i. Relative quantitation may be achieved by:
    1. Determining increased or decreased presence of the IGF-1R protein by comparing the SRM/MRM signature peak area from a given IGF-1R peptide detected in a Liquid Tissue™ lysate from one formalin fixed biological sample to the same SRM/MRM signature peak area of the same IGF-1R fragment peptide in at least a second, third, fourth or more Liquid Tissue™ lysates from least a second, third, fourth or more formalin fixed biological samples
    2. Determining increased or decreased presence of the IGF-1R protein by comparing the SRM/MRM signature peak area from a given IGF-1R peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
    3. Determining increased or decreased presence of the IGF-1R protein by comparing the SRM/MRM signature peak area for a given IGF-1R peptide to the SRM/MRM signature peak areas from other fragment peptides derived from different proteins within the same Liquid Tissue™ sate from the formalin fixed biological sample in order to normalize changing levels of IGF-1R protein to levels of other proteins that do not change their levels of expression under various cellular conditions.
    4. These assays can be applied to both unmodified fragment peptides and for modified fragment peptides of the IGF-1R protein, where the modifications include but are not limited to phosphorylation and/or glycosylation, and where the relative levels of modified peptides are determined in the same manner as determining relative amounts of unmodified peptides.
  ii. Absolute quantitation of a given peptide may be achieved by comparing the SRM/MRM signature peak area for a given fragment peptide from the IGF-1R protein in an individual biological sample to the SRM/MRM signature peak area of an internal fragment peptide standard spiked into the protein lysate from the biological sample
    1. The internal standard is a labeled synthetic version of the fragment peptide from the IGF-1R protein that is being interrogated. This standard is spiked into a sample in known amounts, and the SRM/MRM signature peak area can be determined for both the internal fragment peptide standard and the native fragment peptide in the biological sample separately, followed by comparison of both peak areas
    2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Apply Fragment Peptide Quantitation to Cancer Diagnosis and Treatment
  a. Perform relative and/or absolute quantitation of fragment peptide levels of the IGF-1R protein and demonstrate that the previously-determined association, as well understood in the field of cancer, of IGF-1R protein expression to the stage/grade/status of cancer in patient tumor tissue is confirmed
  b. Perform relative and/or absolute quantitation of fragment peptide levels of the IGF-1R protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy FIG. 1 shows an example of a single SRM/MRM assay performed on Liquid Tissue™ lysates from formalin fixed cancer tissue. An SRM/MRM assay was developed for a single peptide for quantitation of the IGF-1R protein on a triplequadrupole mass spectrometer. Specific and unique characteristics of the IGF-1R peptide GNLLINIR, SEQ ID NO.: 1, were developed by analysis of all IGF-1R peptides on both an ion trap and triple quadrupole mass spectrometers. That information includes the monoisotopic mass of the peptide, its precursor charge state, the precursor m/z value, the transition m/z values of the precursor, and the ion types of each of the identified transitions. That information must be determined experimentally for each and every candidate SRM/MRM peptide directly in Liquid Tissue™ lysates from formalin fixed tissue; because, interestingly, not all peptides from the IGF-1R protein can be detected in such lysates using SRM/MRM as described herein, indicating that IGF-1R peptides not detected cannot be considered candidate peptides for developing an SRM/MRM assay for use in quantitating peptides/proteins directly in Liquid Tissue™ lysates from formalin fixed tissue.

As shown in FIG. 1A, this particular SRM/MRM assay was developed for this specific IGF-1R peptide and was performed on a triple quadrupole mass spectrometer. A control protein lysate where the peptide was known to be present in large amounts was analyzed because this lysate was prepared from a mouse xenograft tumor that resulted from injection of a human-derived cancer cell line into a nude mouse. Thus this xenograft tumor was the positive control. The experimental sample in this experiment was a Liquid Tissue™ protein lysate prepared from standard formalin fixed, paraffin embedded human cancer tissue. Data from the assay indicates the presence of the unique SRM/MRM signature peak for this IGF-1R peptide in both the control sample (top chromatograph) and the experimental sample (bottom chromatograph). By comparing the SRM/MRM signature peak area between these 2 samples generates relative quantitative measure for the IGF-1R protein between 2 different biological samples.

FIG. 1B shows quantitative measurement of the above-mentioned peptide across a collection of seven (7) formalin fixed cancer tissues using an internal standard to achieve absolute quantitation of the IGF-1R protein across a cohort of cancer-derived patient samples. These data indicate absolute amounts of this IGF-1R peptide as a function of molar amount of the peptide per microgram of protein lysate analyzed. Assessment of IGF-1R protein levels in tissues based on analysis of formalin fixed patient-derived tissue can provide diagnostic, prognostic, and therapeutically-relevant information about each particular patient. In one embodiment, this disclosure describes a method for measuring the level of the IGF-1R protein in a biological sample, comprising detecting and/or quantifying the amount of one or more modified or unmodified IGF-1R fragment peptides in a protein digest prepared from said biological sample using mass spectrometry; and calculating the level of modified or unmodified IGF-1R protein in said sample; and wherein said level is a relative level or an absolute level. In a related embodiment, quantifying one or more IGF-1R fragment peptides comprises determining the amount of the each of the IGF-1R fragment peptides in a biological sample by comparison to an added internal standard peptide of known amount, wherein each of the IGF-1R fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the IGF-1R protein in a biological sample described herein (or fragment peptides as surrogates thereof) may be used as a diagnostic indicator of cancer in a patient or subject. In one embodiment, the results from measurements of the level of the IGF-1R protein may be employed to determine the diagnostic stage/grade/status of a cancer by correlating (e.g., comparing) the level of IGF-1R receptor found in a tissue with the level of that protein found in normal and/or cancerous or precancerous tissues.

The invention claimed is:

1. A method for measuring the level of the human Insulin-Like Growth Factor 1 Receptor (IGF-1R) protein in a human biological sample of formalin-fixed tissue, comprising detecting and/or quantifying the amount of an IGF-1R fragment peptide in a protein digest prepared from said human biological sample using mass spectrometry; and calculating the level of IGF-1R protein in said sample;
wherein the IGF-1R fragment peptide is SEQ ID NO:1, and wherein said level is a relative level or an absolute level.

2. The method of claim 1, further comprising the step of fractionating said protein digest prior to detecting and/or quantifying the amount of said IGF-1R fragment peptide.

3. The method of claim 1, wherein said protein digest comprises a protease digest.

4. The method of claim 1, wherein the tissue is paraffin-embedded tissue.

5. The method of claim 1, wherein the tissue is obtained from a tumor.

6. The method of claim 1, further comprising quantifying said IGF-1R fragment peptide.

7. The method of claim 6, wherein quantifying said IGF-1R fragment peptide comprises comparing the amount of said IGF-1R fragment peptide in one biological sample to the amount of the same IGF-1R fragment peptide in a different and separate biological sample.

8. The method of claim 7, wherein quantifying said IGF-1R fragment peptide comprises determining the amount of said IGF-1R fragment peptide in a biological sample by comparison to an added internal standard peptide of known amount, wherein said IGF-1R fragment peptide in the biological sample is compared to an internal standard peptide having the same amino acid sequence; and wherein the internal standard peptide is an isotopically labeled peptide.

9. The method of claim 1, wherein detecting and/or quantifying the amount of said IGF-1R fragment peptide in the protein digest indicates the presence of modified or unmodified IGF-1R protein and an association with cancer in the subject.

10. The method of claim 9, further comprising correlating the results of said detecting and/or quantifying the amount of said IGF-1R fragment peptide, or the level of said IGF-1R protein to the diagnostic stage/grade/status of the cancer.

11. The method of claim 10, wherein correlating the results of said detecting and/or quantifying the amount of said IGF-1R fragment peptide, or the level of said IGF-1R protein to the diagnostic stage/grade/status of the cancer is combined with detecting and/or quantifying the amount of other proteins or peptides from other proteins in a multiplex format to provide additional information about the diagnostic stage/grade/status of the cancer.

12. The method of claim 1, further comprising administering to the patient from which said biological sample was obtained a therapeutically effective amount of a therapeutic agent, wherein the therapeutic agent and/or amount of the therapeutic agent administered is based upon the amount of said IGF-1R fragment peptide or the level of IGF-1R protein.

13. The method of claim 1, wherein therapeutic agents bind the IGF-1R protein and/or inhibit its biological activity.

* * * * *

SEQUENCE LISTING

```
<160> NUMBER OF SEQ ID NOS: 78

<210> SEQ ID NO 1
<211> LENGTH: 8
<212> TYPE: PRT
<213> ORGANISM: Artificial Sequence
<220> FEATURE:
<223> OTHER INFORMATION: IGF-1R peptide

<400> SEQUENCE: 1

Gly Asn Leu Leu Ile Asn Ile Arg
1               5

<210> SEQ ID NO 2
<211> LENGTH: 11
<212> TYPE: PRT
<213> ORGANISM: Artificial Sequence
<220> FEATURE:
<223> OTHER INFORMATION: IGF-1R peptide

<400> SEQUENCE: 2

Ala Gly Lys Met Tyr Phe Ala Phe Asn Pro Lys
1               5                   10

<210> SEQ ID NO 3
<211> LENGTH: 23
<212> TYPE: PRT
<213> ORGANISM: Artificial Sequence
<220> FEATURE:
<223> OTHER INFORMATION: IGF-1R peptide

<400> SEQUENCE: 3

Ala Val Thr Leu Thr Met Val Glu Asn Asp His Ile Arg Gly Ala Lys
1               5                   10                  15

Ser Glu Ile Leu Tyr Ile Arg
            20

<210> SEQ ID NO 4
<211> LENGTH: 12
<212> TYPE: PRT
<213> ORGANISM: Artificial Sequence
<220> FEATURE:
<223> OTHER INFORMATION: IGF-1R peptide

<400> SEQUENCE: 4

Asp Val Glu Pro Gly Ile Leu Leu His Gly Leu Lys
1               5                   10
```

```
<210> SEQ ID NO 5
<211> LENGTH: 18
<212> TYPE: PRT
<213> ORGANISM: Artificial Sequence
<220> FEATURE:
<223> OTHER INFORMATION: IGF-1R peptide

<400> SEQUENCE: 5

Glu Cys Gly Asp Leu Cys Pro Gly Thr Met Glu Glu Lys Pro Met Cys
1               5                   10                  15

Glu Lys

<210> SEQ ID NO 6
<211> LENGTH: 6
<212> TYPE: PRT
<213> ORGANISM: Artificial Sequence
<220> FEATURE:
<223> OTHER INFORMATION: IGF-1R peptide

<400> SEQUENCE: 6

Glu Glu Ala Glu Tyr Arg
1               5

<210> SEQ ID NO 7
<211> LENGTH: 15
<212> TYPE: PRT
<213> ORGANISM: Artificial Sequence
<220> FEATURE:
<223> OTHER INFORMATION: IGF-1R peptide

<400> SEQUENCE: 7

Glu Arg Thr Val Ile Ser Asn Leu Arg Pro Phe Thr Leu Tyr Arg
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 8

Gly Pro Cys Cys Ala Cys Pro Lys Thr Glu Ala Glu Lys Gln Ala Glu
1               5                   10                  15

Lys

<210> SEQ ID NO 9
<211> LENGTH: 14
<212> TYPE: PRT
<213> ORGANISM: Artificial Sequence
<220> FEATURE:
<223> OTHER INFORMATION: IGF-1R peptide

<400> SEQUENCE: 9

Gly Val Val Lys Asp Glu Pro Glu Thr Arg Val Ala Ile Lys
1               5                   10

<210> SEQ ID NO 10
<211> LENGTH: 21
<212> TYPE: PRT
<213> ORGANISM: Artificial Sequence
<220> FEATURE:
<223> OTHER INFORMATION: IGF-1R peptide

<400> SEQUENCE: 10

Ile Pro Ile Arg Lys Tyr Ala Asp Gly Thr Ile Asp Ile Glu Glu Val
```

```
                1               5                   10                  15
Thr Glu Asn Pro Lys
                20

<210> SEQ ID NO 11
<211> LENGTH: 21
<212> TYPE: PRT
<213> ORGANISM: Artificial Sequence
<220> FEATURE:
<223> OTHER INFORMATION: IGF-1R peptide

<400> SEQUENCE: 11

Lys Thr Lys Thr Ile Asp Ser Val Thr Ser Ala Gln Met Leu Gln Gly
1               5                   10                  15

Cys Thr Ile Phe Lys
                20

<210> SEQ ID NO 12
<211> LENGTH: 18
<212> TYPE: PRT
<213> ORGANISM: Artificial Sequence
<220> FEATURE:
<223> OTHER INFORMATION: IGF-1R peptide

<400> SEQUENCE: 12

Leu Cys Val Ser Glu Ile Tyr Arg Met Glu Glu Val Thr Gly Thr Lys
1               5                   10                  15

Gly Arg

<210> SEQ ID NO 13
<211> LENGTH: 24
<212> TYPE: PRT
<213> ORGANISM: Artificial Sequence
<220> FEATURE:
<223> OTHER INFORMATION: IGF-1R peptide

<400> SEQUENCE: 13

Leu Phe Tyr Asn Tyr Ala Leu Val Ile Phe Glu Met Thr Asn Leu Lys
1               5                   10                  15

Asp Ile Gly Leu Tyr Asn Leu Arg
                20

<210> SEQ ID NO 14
<211> LENGTH: 12
<212> TYPE: PRT
<213> ORGANISM: Artificial Sequence
<220> FEATURE:
<223> OTHER INFORMATION: IGF-1R peptide

<400> SEQUENCE: 14

Leu Asn Arg Leu Asn Pro Gly Asn Tyr Thr Ala Arg
1               5                   10

<210> SEQ ID NO 15
<211> LENGTH: 19
<212> TYPE: PRT
<213> ORGANISM: Artificial Sequence
<220> FEATURE:
<223> OTHER INFORMATION: IGF-1R peptide

<400> SEQUENCE: 15

Met Ile Gln Met Ala Gly Glu Ile Ala Asp Gly Met Ala Tyr Leu Asn
1               5                   10                  15

Ala Asn Lys
```

```
<210> SEQ ID NO 16
<211> LENGTH: 28
<212> TYPE: PRT
<213> ORGANISM: Artificial Sequence
<220> FEATURE:
<223> OTHER INFORMATION: IGF-1R peptide

<400> SEQUENCE: 16

Asn Ala Asp Leu Cys Tyr Leu Ser Thr Val Asp Trp Ser Leu Ile Leu
1               5                   10                  15

Asp Ala Val Ser Asn Asn Tyr Ile Val Gly Asn Lys
            20                  25

<210> SEQ ID NO 17
<211> LENGTH: 13
<212> TYPE: PRT
<213> ORGANISM: Artificial Sequence
<220> FEATURE:
<223> OTHER INFORMATION: IGF-1R peptide

<400> SEQUENCE: 17

Pro Asp Asn Cys Pro Asp Met Leu Phe Glu Leu Met Arg
1               5                   10

<210> SEQ ID NO 18
<211> LENGTH: 21
<212> TYPE: PRT
<213> ORGANISM: Artificial Sequence
<220> FEATURE:
<223> OTHER INFORMATION: IGF-1R peptide

<400> SEQUENCE: 18

Pro Met Cys Glu Lys Thr Thr Ile Asn Asn Glu Tyr Asn Tyr Arg Cys
1               5                   10                  15

Trp Thr Thr Asn Arg
            20

<210> SEQ ID NO 19
<211> LENGTH: 16
<212> TYPE: PRT
<213> ORGANISM: Artificial Sequence
<220> FEATURE:
<223> OTHER INFORMATION: IGF-1R peptide

<400> SEQUENCE: 19

Pro Pro Lys Glu Cys Gly Asp Leu Cys Pro Gly Thr Met Glu Glu Lys
1               5                   10                  15

<210> SEQ ID NO 20
<211> LENGTH: 32
<212> TYPE: PRT
<213> ORGANISM: Artificial Sequence
<220> FEATURE:
<223> OTHER INFORMATION: IGF-1R peptide

<400> SEQUENCE: 20

Ser Glu Ile Leu Tyr Ile Arg Thr Asn Ala Ser Val Pro Ser Ile Pro
1               5                   10                  15

Leu Asp Val Leu Ser Ala Ser Asn Ser Ser Ser Gln Leu Ile Val Lys
            20                  25                  30

<210> SEQ ID NO 21
<211> LENGTH: 15
<212> TYPE: PRT
<213> ORGANISM: Artificial Sequence
<220> FEATURE:
```

<223> OTHER INFORMATION: IGF-1R peptide

<400> SEQUENCE: 21

Thr Glu Ala Glu Lys Gln Ala Glu Lys Glu Glu Ala Glu Tyr Arg
1               5                   10                  15

<210> SEQ ID NO 22
<211> LENGTH: 21
<212> TYPE: PRT
<213> ORGANISM: Artificial Sequence
<220> FEATURE:
<223> OTHER INFORMATION: IGF-1R peptide

<400> SEQUENCE: 22

Thr Glu Val Cys Gly Gly Glu Lys Gly Pro Cys Cys Ala Cys Pro Lys
1               5                   10                  15

Thr Glu Ala Glu Lys
            20

<210> SEQ ID NO 23
<211> LENGTH: 35
<212> TYPE: PRT
<213> ORGANISM: Artificial Sequence
<220> FEATURE:
<223> OTHER INFORMATION: IGF-1R peptide

<400> SEQUENCE: 23

Thr Gly Tyr Glu Asn Phe Ile His Leu Ile Ile Ala Leu Pro Val Ala
1               5                   10                  15

Val Leu Leu Ile Val Gly Gly Leu Val Ile Met Leu Tyr Val Phe His
            20                  25                  30

Arg Lys Arg
        35

<210> SEQ ID NO 24
<211> LENGTH: 18
<212> TYPE: PRT
<213> ORGANISM: Artificial Sequence
<220> FEATURE:
<223> OTHER INFORMATION: IGF-1R peptide

<400> SEQUENCE: 24

Thr Ile Asp Ser Val Thr Ser Ala Gln Met Leu Gln Gly Cys Thr Ile
1               5                   10                  15

Phe Lys

<210> SEQ ID NO 25
<211> LENGTH: 28
<212> TYPE: PRT
<213> ORGANISM: Artificial Sequence
<220> FEATURE:
<223> OTHER INFORMATION: IGF-1R peptide

<400> SEQUENCE: 25

Thr Lys Thr Ile Asp Ser Val Thr Ser Ala Gln Met Leu Gln Gly Cys
1               5                   10                  15

Thr Ile Phe Lys Gly Asn Leu Leu Ile Asn Ile Arg
            20                  25

<210> SEQ ID NO 26
<211> LENGTH: 19
<212> TYPE: PRT
<213> ORGANISM: Artificial Sequence
<220> FEATURE:
<223> OTHER INFORMATION: IGF-1R peptide

```
<400> SEQUENCE: 26

Thr Thr Ile Asn Asn Glu Tyr Asn Tyr Arg Cys Trp Thr Thr Asn Arg
1               5                   10                  15

Cys Gln Lys

<210> SEQ ID NO 27
<211> LENGTH: 18
<212> TYPE: PRT
<213> ORGANISM: Artificial Sequence
<220> FEATURE:
<223> OTHER INFORMATION: IGF-1R peptide

<400> SEQUENCE: 27

Val Phe Glu Asn Phe Leu His Asn Ser Ile Phe Val Pro Arg Pro Glu
1               5                   10                  15

Arg Lys

<210> SEQ ID NO 28
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 28

Trp Asn Pro Pro Ser Leu Pro Asn Gly Asn Leu Ser Tyr Tyr Ile Val
1               5                   10                  15

Arg

<210> SEQ ID NO 29
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 29

Trp Pro Glu Pro Glu Asn Pro Asn Gly Leu Ile Leu Met Tyr Glu Ile
1               5                   10                  15

Lys

<210> SEQ ID NO 30
<211> LENGTH: 24
<212> TYPE: PRT
<213> ORGANISM: Artificial Sequence
<220> FEATURE:
<223> OTHER INFORMATION: IGF-1R peptide

<400> SEQUENCE: 30

Tyr Ala Asp Gly Thr Ile Asp Ile Glu Glu Val Thr Glu Asn Pro Lys
1               5                   10                  15

Thr Glu Val Cys Gly Gly Glu Lys
            20

<210> SEQ ID NO 31
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 31

Tyr Gly Gly Ala Lys Leu Asn Arg Leu Asn Pro Gly Asn Tyr Thr Ala
```

```
1               5                  10                 15
Arg

<210> SEQ ID NO 32
<211> LENGTH: 14
<212> TYPE: PRT
<213> ORGANISM: Artificial Sequence
<220> FEATURE:
<223> OTHER INFORMATION: IGF-1R peptide

<400> SEQUENCE: 32

Tyr Gly Ser Gln Val Glu Asp Gln Arg Glu Cys Val Ser Arg
1               5                  10

<210> SEQ ID NO 33
<211> LENGTH: 30
<212> TYPE: PRT
<213> ORGANISM: Artificial Sequence
<220> FEATURE:
<223> OTHER INFORMATION: IGF-1R peptide

<400> SEQUENCE: 33

Ala Cys Thr Glu Asn Asn Glu Cys Cys His Pro Glu Cys Leu Gly Ser
1               5                  10                 15

Cys Ser Ala Pro Asp Asn Asp Thr Ala Cys Val Ala Cys Arg
            20                 25                 30

<210> SEQ ID NO 34
<211> LENGTH: 16
<212> TYPE: PRT
<213> ORGANISM: Artificial Sequence
<220> FEATURE:
<223> OTHER INFORMATION: IGF-1R peptide

<400> SEQUENCE: 34

Asp Leu Ala Ala Arg Asn Cys Met Val Ala Glu Asp Phe Thr Val Lys
1               5                  10                 15

<210> SEQ ID NO 35
<211> LENGTH: 15
<212> TYPE: PRT
<213> ORGANISM: Artificial Sequence
<220> FEATURE:
<223> OTHER INFORMATION: IGF-1R peptide

<400> SEQUENCE: 35

Asp Leu Ile Ser Phe Thr Val Tyr Tyr Lys Glu Ala Pro Phe Lys
1               5                  10                 15

<210> SEQ ID NO 36
<211> LENGTH: 23
<212> TYPE: PRT
<213> ORGANISM: Artificial Sequence
<220> FEATURE:
<223> OTHER INFORMATION: IGF-1R peptide

<400> SEQUENCE: 36

Glu Lys Ile Thr Met Ser Arg Glu Leu Gly Gln Gly Ser Phe Gly Met
1               5                  10                 15

Val Tyr Glu Gly Val Ala Lys
            20

<210> SEQ ID NO 37
<211> LENGTH: 20
<212> TYPE: PRT
<213> ORGANISM: Artificial Sequence
```

```
<220> FEATURE:
<223> OTHER INFORMATION: IGF-1R peptide

<400> SEQUENCE: 37

Glu Leu Gly Gln Gly Ser Phe Gly Met Val Tyr Glu Gly Val Ala Lys
1               5                   10                  15

Gly Val Val Lys
            20

<210> SEQ ID NO 38
<211> LENGTH: 15
<212> TYPE: PRT
<213> ORGANISM: Artificial Sequence
<220> FEATURE:
<223> OTHER INFORMATION: IGF-1R peptide

<400> SEQUENCE: 38

Phe Pro Lys Leu Thr Val Ile Thr Glu Tyr Leu Leu Leu Phe Arg
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: IGF-1R peptide

<400> SEQUENCE: 39

Phe Val Met Glu Gly Gly Leu Leu Asp Lys
1               5                   10

<210> SEQ ID NO 40
<211> LENGTH: 23
<212> TYPE: PRT
<213> ORGANISM: Artificial Sequence
<220> FEATURE:
<223> OTHER INFORMATION: IGF-1R peptide

<400> SEQUENCE: 40

Gly Asn Asn Ile Ala Ser Glu Leu Glu Asn Phe Met Gly Leu Ile Glu
1               5                   10                  15

Val Val Thr Gly Tyr Val Lys
            20

<210> SEQ ID NO 41
<211> LENGTH: 27
<212> TYPE: PRT
<213> ORGANISM: Artificial Sequence
<220> FEATURE:
<223> OTHER INFORMATION: IGF-1R peptide

<400> SEQUENCE: 41

Gly Trp Lys Leu Phe Tyr Asn Tyr Ala Leu Val Ile Phe Glu Met Thr
1               5                   10                  15

Asn Leu Lys Asp Ile Gly Leu Tyr Asn Leu Arg
            20                  25

<210> SEQ ID NO 42
<211> LENGTH: 18
<212> TYPE: PRT
<213> ORGANISM: Artificial Sequence
<220> FEATURE:
<223> OTHER INFORMATION: IGF-1R peptide

<400> SEQUENCE: 42

His Tyr Tyr Tyr Ala Gly Val Cys Val Pro Ala Cys Pro Pro Asn Thr
```

```
                  1               5              10              15
Tyr Arg

<210> SEQ ID NO 43
<211> LENGTH: 24
<212> TYPE: PRT
<213> ORGANISM: Artificial Sequence
<220> FEATURE:
<223> OTHER INFORMATION: IGF-1R peptide

<400> SEQUENCE: 43

Ile Asp Ile His Ser Cys Asn His Glu Ala Glu Lys Leu Gly Cys Ser
1               5                  10                  15

Ala Ser Asn Phe Val Phe Ala Arg
            20

<210> SEQ ID NO 44
<211> LENGTH: 7
<212> TYPE: PRT
<213> ORGANISM: Artificial Sequence
<220> FEATURE:
<223> OTHER INFORMATION: IGF-1R peptide

<400> SEQUENCE: 44

Tyr Arg Pro Pro Asp Tyr Arg
1               5

<210> SEQ ID NO 45
<211> LENGTH: 6
<212> TYPE: PRT
<213> ORGANISM: Artificial Sequence
<220> FEATURE:
<223> OTHER INFORMATION: IGF-1R peptide

<400> SEQUENCE: 45

Lys Tyr Gly Gly Ala Lys
1               5

<210> SEQ ID NO 46
<211> LENGTH: 26
<212> TYPE: PRT
<213> ORGANISM: Artificial Sequence
<220> FEATURE:
<223> OTHER INFORMATION: IGF-1R peptide

<400> SEQUENCE: 46

Leu Glu Asn Cys Thr Val Ile Glu Gly Tyr Leu His Ile Leu Leu Ile
1               5                  10                  15

Ser Lys Ala Glu Asp Tyr Arg Ser Tyr Arg
            20                  25

<210> SEQ ID NO 47
<211> LENGTH: 32
<212> TYPE: PRT
<213> ORGANISM: Artificial Sequence
<220> FEATURE:
<223> OTHER INFORMATION: IGF-1R peptide

<400> SEQUENCE: 47

Leu Asn Pro Gly Asn Tyr Thr Ala Arg Ile Gln Ala Thr Ser Leu Ser
1               5                  10                  15

Gly Asn Gly Ser Trp Thr Asp Pro Val Phe Phe Tyr Val Gln Ala Lys
            20                  25                  30

<210> SEQ ID NO 48
```

```
<211> LENGTH: 13
<212> TYPE: PRT
<213> ORGANISM: Artificial Sequence
<220> FEATURE:
<223> OTHER INFORMATION: IGF-1R peptide

<400> SEQUENCE: 48

Met Glu Glu Val Thr Gly Thr Lys Gly Arg Gln Ser Lys
1               5                   10

<210> SEQ ID NO 49
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 49

Asn Gly Ser Gln Ser Met Tyr Cys Ile Pro Cys Glu Gly Pro Cys Pro
1               5                   10                  15

Lys

<210> SEQ ID NO 50
<211> LENGTH: 23
<212> TYPE: PRT
<213> ORGANISM: Artificial Sequence
<220> FEATURE:
<223> OTHER INFORMATION: IGF-1R peptide

<400> SEQUENCE: 50

Asn Gly Ser Gln Ser Met Tyr Cys Ile Pro Cys Glu Gly Pro Cys Pro
1               5                   10                  15

Lys Val Cys Glu Glu Glu Lys
            20

<210> SEQ ID NO 51
<211> LENGTH: 8
<212> TYPE: PRT
<213> ORGANISM: Artificial Sequence
<220> FEATURE:
<223> OTHER INFORMATION: IGF-1R peptide

<400> SEQUENCE: 51

Asn Ile Thr Arg Gly Ala Ile Arg
1               5

<210> SEQ ID NO 52
<211> LENGTH: 5
<212> TYPE: PRT
<213> ORGANISM: Artificial Sequence
<220> FEATURE:
<223> OTHER INFORMATION: IGF-1R peptide

<400> SEQUENCE: 52

Asn Asn Gly Glu Arg
1               5

<210> SEQ ID NO 53
<211> LENGTH: 22
<212> TYPE: PRT
<213> ORGANISM: Artificial Sequence
<220> FEATURE:
<223> OTHER INFORMATION: IGF-1R peptide

<400> SEQUENCE: 53

Asn Asn Gly Glu Arg Ala Ser Cys Glu Ser Asp Val Leu His Phe Thr
1               5                   10                  15
```

Ser Thr Thr Thr Ser Lys
            20

<210> SEQ ID NO 54
<211> LENGTH: 9
<212> TYPE: PRT
<213> ORGANISM: Artificial Sequence
<220> FEATURE:
<223> OTHER INFORMATION: IGF-1R peptide

<400> SEQUENCE: 54

Gln Pro Gln Asp Gly Tyr Leu Tyr Arg
1               5

<210> SEQ ID NO 55
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 55

Gln Pro Gln Asp Gly Tyr Leu Tyr Arg His Asn Tyr Cys Ser Lys Asp
1               5                   10                  15

Lys

<210> SEQ ID NO 56
<211> LENGTH: 14
<212> TYPE: PRT
<213> ORGANISM: Artificial Sequence
<220> FEATURE:
<223> OTHER INFORMATION: IGF-1R peptide

<400> SEQUENCE: 56

Gln Ser Lys Gly Asp Ile Asn Thr Arg Asn Asn Gly Glu Arg
1               5                   10

<210> SEQ ID NO 57
<211> LENGTH: 26
<212> TYPE: PRT
<213> ORGANISM: Artificial Sequence
<220> FEATURE:
<223> OTHER INFORMATION: IGF-1R peptide

<400> SEQUENCE: 57

Arg Gly Asn Asn Ile Ala Ser Glu Leu Glu Asn Phe Met Gly Leu Ile
1               5                   10                  15

Glu Val Val Thr Gly Tyr Val Lys Ile Arg
            20                  25

<210> SEQ ID NO 58
<211> LENGTH: 28
<212> TYPE: PRT
<213> ORGANISM: Artificial Sequence
<220> FEATURE:
<223> OTHER INFORMATION: IGF-1R peptide

<400> SEQUENCE: 58

Ser Arg Asn Thr Thr Ala Ala Asp Thr Tyr Asn Ile Thr Asp Pro Glu
1               5                   10                  15

Glu Leu Glu Thr Glu Tyr Pro Phe Phe Glu Ser Arg
            20                  25

<210> SEQ ID NO 59
<211> LENGTH: 25

```
<212> TYPE: PRT
<213> ORGANISM: Artificial Sequence
<220> FEATURE:
<223> OTHER INFORMATION: IGF-1R peptide

<400> SEQUENCE: 59

Thr Asn Ala Ser Val Pro Ser Ile Pro Leu Asp Val Leu Ser Ala Ser
1               5                   10                  15

Asn Ser Ser Ser Gln Leu Ile Val Lys
            20                  25

<210> SEQ ID NO 60
<211> LENGTH: 13
<212> TYPE: PRT
<213> ORGANISM: Artificial Sequence
<220> FEATURE:
<223> OTHER INFORMATION: IGF-1R peptide

<400> SEQUENCE: 60

Thr Val Ile Ser Asn Leu Arg Pro Phe Thr Leu Tyr Arg
1               5                   10

<210> SEQ ID NO 61
<211> LENGTH: 21
<212> TYPE: PRT
<213> ORGANISM: Artificial Sequence
<220> FEATURE:
<223> OTHER INFORMATION: IGF-1R peptide

<400> SEQUENCE: 61

Val Ala Gly Leu Glu Ser Leu Gly Asp Leu Phe Pro Asn Leu Thr Val
1               5                   10                  15

Ile Arg Gly Trp Lys
            20

<210> SEQ ID NO 62
<211> LENGTH: 17
<212> TYPE: PRT
<213> ORGANISM: Artificial Sequence
<220> FEATURE:
<223> OTHER INFORMATION: IGF-1R peptide

<400> SEQUENCE: 62

Trp Pro Glu Pro Glu Asn Pro Asn Gly Leu Ile Leu Met Tyr Glu Ile
1               5                   10                  15

Lys

<210> SEQ ID NO 63
<211> LENGTH: 10
<212> TYPE: PRT
<213> ORGANISM: Artificial Sequence
<220> FEATURE:
<223> OTHER INFORMATION: IGF-1R peptide

<400> SEQUENCE: 63

Ala Leu Pro Leu Pro Gln Ser Ser Thr Cys
1               5                   10

<210> SEQ ID NO 64
<211> LENGTH: 25
<212> TYPE: PRT
<213> ORGANISM: Artificial Sequence
<220> FEATURE:
<223> OTHER INFORMATION: IGF-1R peptide

<400> SEQUENCE: 64
```

```
Ser Cys Glu Ser Asp Val Leu His Phe Thr Ser Thr Thr Thr Ser Lys
1               5                   10                  15

Asn Arg Ile Ile Ile Thr Trp His Arg
            20                  25
```

<210> SEQ ID NO 65
<211> LENGTH: 7
<212> TYPE: PRT
<213> ORGANISM: Artificial Sequence
<220> FEATURE:
<223> OTHER INFORMATION: IGF-1R peptide

<400> SEQUENCE: 65

```
Ile Ile Ile Thr Trp His Arg
1               5
```

<210> SEQ ID NO 66
<211> LENGTH: 10
<212> TYPE: PRT
<213> ORGANISM: Artificial Sequence
<220> FEATURE:
<223> OTHER INFORMATION: IGF-1R peptide

<400> SEQUENCE: 66

```
Phe Val Met Glu Gly Gly Leu Leu Asp Lys
1               5                   10
```

<210> SEQ ID NO 67
<211> LENGTH: 23
<212> TYPE: PRT
<213> ORGANISM: Artificial Sequence
<220> FEATURE:
<223> OTHER INFORMATION: IGF-1R peptide

<400> SEQUENCE: 67

```
His Tyr Tyr Tyr Ala Gly Val Cys Val Pro Ala Cys Pro Pro Asn Thr
1               5                   10                  15

Tyr Arg Phe Glu Gly Trp Arg
            20
```

<210> SEQ ID NO 68
<211> LENGTH: 26
<212> TYPE: PRT
<213> ORGANISM: Artificial Sequence
<220> FEATURE:
<223> OTHER INFORMATION: IGF-1R peptide

<400> SEQUENCE: 68

```
Asn Asp Tyr Gln Gln Leu Lys Arg Leu Glu Asn Cys Thr Val Ile Glu
1               5                   10                  15

Gly Tyr Leu His Ile Leu Leu Ile Ser Lys
            20                  25
```

<210> SEQ ID NO 69
<211> LENGTH: 24
<212> TYPE: PRT
<213> ORGANISM: Artificial Sequence
<220> FEATURE:
<223> OTHER INFORMATION: IGF-1R peptide

<400> SEQUENCE: 69

```
Asn Gly Ser Gln Ser Met Tyr Cys Ile Pro Cys Glu Gly Pro Cys Pro
1               5                   10                  15

Lys Val Cys Glu Glu Glu Lys Lys
            20
```

```
<210> SEQ ID NO 70
<211> LENGTH: 26
<212> TYPE: PRT
<213> ORGANISM: Artificial Sequence
<220> FEATURE:
<223> OTHER INFORMATION: IGF-1R peptide

<400> SEQUENCE: 70

Asn Thr Thr Ala Ala Asp Thr Tyr Asn Ile Thr Asp Pro Glu Glu Leu
1               5                   10                  15

Glu Thr Glu Tyr Pro Phe Phe Glu Ser Arg
            20                  25

<210> SEQ ID NO 71
<211> LENGTH: 9
<212> TYPE: PRT
<213> ORGANISM: Artificial Sequence
<220> FEATURE:
<223> OTHER INFORMATION: IGF-1R peptide

<400> SEQUENCE: 71

Asp Ile Tyr Glu Thr Asp Tyr Tyr Arg
1               5

<210> SEQ ID NO 72
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (3)..(3)
<223> OTHER INFORMATION: PHOSPHORYLATION

<400> SEQUENCE: 72

Asp Ile Tyr Glu Thr Asp Tyr Tyr Arg
1               5

<210> SEQ ID NO 73
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 73

Asp Ile Tyr Glu Thr Asp Tyr Tyr Arg
1               5

<210> SEQ ID NO 74
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
```

```
<222> LOCATION: (8)..(8)
<223> OTHER INFORMATION: PHOSPHORYLATION

<400> SEQUENCE: 74

Asp Ile Tyr Glu Thr Asp Tyr Tyr Arg
1               5

<210> SEQ ID NO 75
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 75

Asp Ile Tyr Glu Thr Asp Tyr Tyr Arg
1               5

<210> SEQ ID NO 76
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (7)..(7)
<223> OTHER INFORMATION: PHOSPHORYLATION

<400> SEQUENCE: 76

Asp Ile Tyr Glu Thr Asp Tyr Tyr Arg
1               5

<210> SEQ ID NO 77
<211> LENGTH: 9
<212> TYPE: PRT
<213> ORGANISM: Artificial Sequence
<220> FEATURE:
<223> OTHER INFORMATION: IGF-1R peptide
<220> FEATURE:
<221> NAME/KEY: MOD_RES
<222> LOCATION: (8)..(8)
<223> OTHER INFORMATION: PHOSPHORYLATION

<400> SEQUENCE: 77

Asp Ile Tyr Glu Thr Asp Tyr Tyr Arg
1               5

<210> SEQ ID NO 78
<211> LENGTH: 9
<212> TYPE: PRT
<213> ORGANISM: Artificial Sequence
<220> FEATURE:
<223> OTHER INFORMATION: IGF-1R peptides
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
```

-continued

```
<222> LOCATION: (8)..(8)
<223> OTHER INFORMATION: PHOSPHORYLATION

<400> SEQUENCE: 78

Asp Ile Tyr Glu Thr Asp Tyr Tyr Arg
1               5
```